US011317880B2

(12) United States Patent
Achatz et al.

(10) Patent No.: US 11,317,880 B2
(45) Date of Patent: May 3, 2022

(54) DETERMINING ROTATIONAL ORIENTATION OF A DEEP BRAIN STIMULATION ELECTRODE IN A THREE-DIMENSIONAL IMAGE

(71) Applicant: Brainlab AG, Munich (DE)

(72) Inventors: Stefan Achatz, Freising (DE); Swen Woerlein, Munich (DE)

(73) Assignee: BRAINLAB AG, Munich (DE)

( * ) Notice: Subject to any disclaimer, the term of this patent is extended or adjusted under 35 U.S.C. 154(b) by 378 days.

(21) Appl. No.: 15/761,752

(22) PCT Filed: Jan. 24, 2017

(86) PCT No.: PCT/EP2017/051426
§ 371 (c)(1),
(2) Date: Mar. 20, 2018

(87) PCT Pub. No.: WO2018/137759
PCT Pub. Date: Aug. 2, 2018

(65) Prior Publication Data
US 2020/0237326 A1    Jul. 30, 2020

(51) Int. Cl.
*A61B 6/12*    (2006.01)
*A61B 6/03*    (2006.01)
(Continued)

(52) U.S. Cl.
CPC ............ *A61B 6/12* (2013.01); *A61B 6/032* (2013.01); *A61B 6/5247* (2013.01); *G06T 7/13* (2017.01);
(Continued)

(58) Field of Classification Search
CPC ......... A61B 6/12; A61B 6/032; A61B 6/5247; G06T 7/13; G06T 7/168;
(Continued)

(56) References Cited

U.S. PATENT DOCUMENTS 8,849,375 B2    9/2014    Baumgart et al.
8,995,731 B2 *  3/2015    Joglekar ............... A61B 6/12
                                                    382/128
(Continued)

FOREIGN PATENT DOCUMENTS

DE    102010027692    1/2012
WO    WO2010092512 A1    8/2010
WO    WO2017040573 A1    3/2017

OTHER PUBLICATIONS

International Search Report and Written Opinion issued in PCT Application No. PCT/EP2017/051426 dated Oct. 23, 2017.
(Continued)

*Primary Examiner* — Joseph M Santos Rodriguez
*Assistant Examiner* — Kaitlyn E Selmer
(74) *Attorney, Agent, or Firm* — Middleton Reutlinger

(57) ABSTRACT

Disclosed is a computer-implemented medical data processing method for determining an orientation of an electrode, the electrode being configured for electrically stimulating an anatomical structure of a patient and comprising a rotational orientation marker, the method comprising executing, on at least one processor of at least one computer, steps of: a) acquiring (S1.1), at the at least one processor, rotational image data describing two-dimensional medical images of the anatomical structure and the electrode, the two-dimensional medical images having been taken with a two-dimensional medical imaging apparatus during rotation of the medical imaging apparatus relative to the anatomical structure, the rotational image data further describing, for each of the two-dimensional medical images, an imaging perspective relative to the anatomical structure associated with the respective two-dimensional medical image; b) determining (S1.2), by the at least one processor and based on the rotational image data, rotational orientation data describing the rotational orientation of the electrode in the
(Continued)

reference system of the two-dimensional medical images; c) acquiring (S1.3), at the at least one processor, tomographic image data describing a set of tomographic medical images of the anatomical structure; d) determining (S1.4), by the at least one processor and based on the rotational image data and the tomographic image data and the rotational orientation data, electrode orientation data describing a rotational orientation of the electrode in a reference system of the tomographic medical image data.

15 Claims, 4 Drawing Sheets

(51) Int. Cl.
*A61B 6/00* (2006.01)
*G06T 7/13* (2017.01)
*G06T 7/168* (2017.01)

(52) U.S. Cl.
CPC .... *G06T 7/168* (2017.01); *G06T 2207/10081* (2013.01); *G06T 2207/10116* (2013.01); *G06T 2207/10124* (2013.01); *G06T 2207/30004* (2013.01); *G06T 2207/30204* (2013.01)

(58) Field of Classification Search
CPC . G06T 2207/10116; G06T 2207/30204; G06T 2207/10081; G06T 2207/10124; G06T 2207/30004

See application file for complete search history.

(56) References Cited

U.S. PATENT DOCUMENTS

| | | | |
|---|---|---|---|
| 2007/0269000 A1* | 11/2007 | Partain | A61B 6/4241 378/37 |
| 2014/0094823 A1* | 4/2014 | Carcieri | A61N 1/37247 606/129 |
| 2015/0283379 A1 | 10/2015 | Venkatesan | |
| 2015/0287198 A1* | 10/2015 | Vilsmeier | G06T 7/0014 382/128 |
| 2016/0019706 A1* | 1/2016 | Otomaru | G06F 3/04845 345/634 |
| 2016/0171692 A1* | 6/2016 | Blumhofer | G06T 7/337 382/128 |

OTHER PUBLICATIONS

Zollei, et al. "2D-3D Rigid Registration of X-Ray Fluoroscopy and CT Images Using Mutual Information and Sparsely Sampled Histogram Estimators" 2001.

* cited by examiner

DETERMINING ROTATIONAL ORIENTATION OF A DEEP BRAIN STIMULATION ELECTRODE IN A THREE-DIMENSIONAL IMAGE

The present invention relates to a computer-implemented medical method for determining an orientation of an electrode. The electrode is for example configured for electrically (for example, electromagnetically) stimulating an anatomical structure of a patient and comprises a rotational orientation marker: The invention also relates to a computer configured to execute a program corresponding to the method and a medical system for determining an orientation of an electrode comprising such a computer.

TECHNICAL BACKGROUND

Directional Deep Brain Stimulation (DBS) leads (also called electrodes) allow for focusing the stimulation towards certain angles of the lead (i.e. electrode). For planning the stimulation or evaluating stimulation effects the knowledge of the correct directional orientation of the lead with respect to the patient anatomy is necessary. The lead is equipped with a rotationally asymmetric marker which was designed to be detected and evaluated by post-operative imaging. Unfortunately, MRI is not eligible due to metal in the leads and CTs are too blurry in order to recognize the marker with sufficient accuracy.

All previous methods do not allow for an automatized, traceable and accurate measurement of the rotational angle defining the rotational angular orientation of the electrode around its longitudinal axis.

The present invention is designed to provide a reliable method for determining the orientation of an electrode in the reference system of a three-dimensional medical image.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method uses rotational x-rays (e.g. from rotational angiography, cone beam CT, C-arm x-ray). On the series of x-ray shots taken while the detector rotates around the head, the lead (electrode) and its marker is clearly visible on the images from different angles. These images allow for determining the angle of the marker with respect to the image plane and/or the reference system of the images. In order to transfer this knowledge into 3D (three-dimensional) patient system, the 2D x-ray images are registered to an anatomical 3D image volume with the help of an automatic algorithm. By means of blending digitally reconstructed radiographs of the 3d image data onto the 2D x-ray images the user can verify the match of 2D and 3D images immediately and assess the accuracy of the calculated orientation angle. Also, the rotational orientation of the lead in the reference system of the 3D image volume can be determined.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented medical method for determining an orientation of an electrode. The electrode is for example configured for electrically (for example, electromagnetically) stimulating an anatomical structure of a patient and comprises a rotational orientation marker.

The electrode may be a directional electrode for deep brain stimulation (a DBS electrode) which comprises different distinct contacts which are located in discrete segments along the longitudinal axis of the electrode and may take the form of a patch not extending entirely around the circumference of the electrode but extending only along an angular sector (a ring segment) around the longitudinal axis of the electrode. The electrode generally takes an elongate, basically cylindrical and in one example rigid shape having a distal end pointing towards the interior of a patient's body and a proximal end pointing towards an exterior of a patient's body. Due to its elongation, the electrode is defined to have a longitudinal axis extending e.g. from proximal end to the distal end of the electrode. The electrode is generally a directional DBS electrode which allows for selective stimulation of only a three-dimensional angular sector in the direction of the respective contact. In order to achieve a desired stimulation of an anatomical structure being or comprising a target region which shall be stimulated, the rotational angular orientation of the directional electrode relative to the position of the anatomical structure (target region) has to be determined so that the anatomical structure (target region) lies in the sector covered by the directional characteristic (emission characteristic) of at least one of the directional contacts of the electrode.

The method according to the first aspect is concerned with determining the angular orientation of the electrode for example relative to a plane in which it is depicted in a two-dimensional medical image, in order to determine, on the basis of further information as explained below, the rotational orientation of the electrode relative to the anatomical structure, for example in a reference system of a three-dimensional image data set depicting both the anatomical structure and the electrode. The angular orientation can be defined as a rotational phase of the electrode (for example, of the orientation marker) in the medical two-dimensional image around a rotational axis defined by the extension of the longitudinal axis of the electrode, for example as a rotational phase of the depicted planar section through the electrode in the image plane of the two-dimensional image relative to the circumferential position of the directional marker on the circumference of the electrode. In other words, the angular orientation is defined as a rotation angle along the circumference of the electrode relative to e.g. the position of the orientation marker on the circumference. In even other words, the angular orientation is defined by the angle (for example, spatial angle, which may be defined in a three-dimensional reference system such as spherical coordinates) between a plane in which at least one of a predetermined (for example, at least one of known or fixed) position of the orientation marker (for example, of its first part) or a radius of the electrode intersecting that position, and the longitudinal axis of the electrode lie on the one hand, and the image plane of the two-dimensional medical image on the other hand. The orientations of those two planes are generally parallel to one another and/or both orientations lie in a common plane. Minor three-dimensional deviations from this spatial relationship between the orientations can be neglected for achieving the effect of the method according to the first aspect. The spatial relationship between the predetermined position of the orientation marker and the remainder of the electrode is predetermined (for example, at least one of known or fixed), for example from electrode template data comprising constructional data describing (for example, defining or representing) the geometry of the electrode. A coordinate transformation between the reference system in which the angular orientation is defined and a coordinate system in which at least one of the remainder of the electrode or the image positions in the two-dimensional medical image are defined is predetermined (for example, at least one of known or fixed). Within the meaning of this disclosure, the term reference system encompasses and generally is equivalent to the term coordinate system. Thus, the rotational orientation of the electrode in the reference system of the two-dimensional medical image (in which positions defining the image contents of the two-dimensional medical image are defined) can be determined from analysing the two-dimensional medical image.

Notably, placement of such an electrode in the human or animal body is not part of the disclosed method. Furthermore, execution of the disclosed method does not require the electrode to be placed while the disclosed method is executed. In other words, the disclosed method according to the first aspect is a method of at least one of operating or controlling a data processing device such as a computer, e.g. by running a corresponding program on the data processing device so as to cause the data processing device to execute the steps of the method according to the first aspect.

The method according to the first aspect is for example a data processing method. The method according to the first aspect comprises executing, on at least one processor of at least one computer (for example at least one computer being part of a deep brain stimulation calibration or tuning system), the following exemplary steps which are executed by the at least one processor.

In a (for example first) exemplary step, rotational image data is acquired which describes (for example, at least one of defines or represents) two-dimensional medical images of (i.e. depicting or showing) the anatomical structure and the electrode. Specifically, the two-dimensional images (for example each) depict both the anatomical structure and the electrode. Generally, the anatomical structure may be any anatomical body part containing at least one nerve fibre which may be electrically (electromagnetically) stimulated (e.g. the anatomical structure comprises, for example is, at least part of the brain), or muscular tissue which may be electrically stimulated to cause e.g. muscular contraction or extension.

The two-dimensional medical images have been or are being taken with a two-dimensional medical imaging apparatus or method such as imaging with a C-arm (C-arm x-ray, also called C-arm radiography), by rotational angiography or cone beam computed x-ray tomography (cone beam CT). For example, the two-dimensional images have been or are being taken during rotation of the medical imaging apparatus relative to the anatomical structure, i.e. each two-dimensional image has been taken at a different rotational position of the medical imaging apparatus relative to the position of the anatomical structure and the electrode, for example such that immediately subsequent positions of the medical imaging apparatus are associated with two-dimensional images taken immediately subsequently in the order of their generation. For example, each two-dimensional medical image is associated with a different imaging perspective (for example, relative to the position of the anatomical structure). The rotational image data further describes, for each of the two-dimensional medical images, an imaging perspective relative to the anatomical structure associated with the respective two-dimensional medical image. The imaging perspective is preferably defines by the position of the medical imaging apparatus which the medical imaging apparatus had relative to the anatomical structure and for example the electrode when the respective two-dimensional image was generated. The step of generating the rotational image data (i.e. conducting the associated imaging procedure) generally is not part of the claimed method and is in one example performed before the method according to the first aspect is executed. The rotational image data is then acquired (read) by the method at a later point in time. However, generation of the rotational image data may in another example of the method be part of the method according to the first aspect.

In a further (for example second) exemplary step, rotational orientation data is determined which describes (for example defines or represents) the rotational orientation of the electrode in the reference system of the two-dimensional medical images (in which positions defining the image contents of the rotational image data are defined). The reference system of the two-dimensional images is for example a reference system used for generating the rotational image data and may be predetermined by the two-dimensional medical imaging apparatus (such as C-arm x-ray device). The rotational orientation data is determined for example based on the rotational image data, for example from the image depiction of the electrode in the respective two-dimensional image. To this end, at least one of the two-dimensional medical images is analysed concerning the image appearance of the orientation marker in the two-dimensional image. In one example, all of the two-dimensional medical images are accordingly analysed. This can be done for example by determining, based on the rotational image data, an image appearance of the orientation marker, for example by at least one of:

- segmenting an image appearance of the electrode in the at least one or each of the two-dimensional medical images;
- edge detection of constituents of the at least one or each of the two-dimensional medical images;
- comparing the image appearance of the electrode in the at least one or each of the two-dimensional medical images to previously acquired and predetermined electrode template data describing constructional data of the electrode (such as at least one of its geometry and the spatial relationship—at least one of position and orientation—between at least one directional contact and the orientation marker).

The rotational orientation of the electrode is then determined from knowledge about the imaging perspective associated with the respective two-dimensional image in the reference system of the two-dimensional medical images, and for example the previously acquired electrode template data, if necessary considering any recalculation of positions or orientations of part of the electrode or spatial relationships described by the electrode template data into the reference system of the two-dimensional images.

In a further example, the for example second exemplary step comprises acquiring predetermined orientation data which describes (for example defines or represents) a predetermined rotational orientation of the electrode in the reference system of the two-dimensional medical images. The position and orientation of the orientation marker relative to the electrode is predetermined (for example, at least one of known or fixed) for example and included in or derivable from the electrode template data which to that end may be acquired by the method according to the first aspect. The predetermined orientation may for example an orientation in which the orientation marker has a predetermined (for example, at least one of known or fixed) appearance in a two-dimensional image. For example, the orientation marker has a first part which covers a circumferential surface along less than 180° of the circumference and for a predetermined (for example, at least one of known or fixed) length (and in a more specific example less than the total length) along the longitudinal axis of the electrode, and for the remaining circumference. In one example, the orientation marker has, at a further position along the longitudinal axis, a further, second part which covers the surface of the electrode at least over the remainder of the circumference). The orientation of the electrode is generally determined by extracting, from the at least one of the two-dimensional medical images, an image appearance of the orientation marker, and comparing it to a predetermined (for example, at least one of known or fixed) image appearance of the orientation marker. For example, the first part has a predetermined thickness if it is two-dimensionally imaged in a specific imaging plane, for example in a plane intersecting both the longitudinal axis of the electrode and representing a mirror plane of symmetry of the orientation marker. This thickness of the image appearance of the first part may define the predetermined orientation of the orientation marker and the electrode. The method then determines, based on the rotational orientation data and the predetermined orientation data, optimal orientation data.

The optimal orientation data describes (for example, defines or represents) the two-dimensional medical image associated with a rotational orientation of the electrode (in the image plane of the two-dimensional medical image) fulfilling a predetermined condition in relation to the predetermined rotational orientation. Within this disclosure, that two-dimensional medical image is also called the optimal two-dimensional medical image, specifically because it is associated with the so-called optimal rotational orientation of the orientation marker when compared to the predetermined orientation. The optimal two-dimensional image is determined for example by comparing the image appearance of the orientation marker in the at least one of the two-dimensional medical images (for example, in each one of the two-dimensional medical images) to the predetermined image appearance of the orientation marker in order to determine whether the image appearance of the orientation marker fulfils a predetermined condition relative to the predetermined image appearance, for example whether its thickness in the at least one two-dimensional medical image is at least within a predetermined (for example, at least one of known or fixed) limit equal to its predetermined thickness. If it is determined that the image appearance of the orientation marker in the at least one of the two-dimensional medical image fulfils the predetermined condition, the associated two-dimensional medical image is determined to be the optimal two-dimensional medical image. If more than one of the two-dimensional medical images is analysed in this manner, and if better fulfilment of the predetermined condition is determined for another one of the two-dimensional medical images, then that other two-dimensional medical image is determined to be the optimal two-dimensional medical image.

In a (for example third) exemplary step, tomographic image data is acquired which describes (for example, defines or represents) a set of tomographic medical images of the anatomical structure. The positions defining the image contents of the tomographic image data are defined in three dimensions (i.e. in a three-dimensional reference system), and the tomographic image data is for example generated before execution of the method according to the first aspect starts. For example, it may be present in the form of a planning image data set used for planning an envisaged medical procedure. The tomographic image data allows for generation of slice images of the anatomical structure from different perspectives including the perspective associated with the optimal two-dimensional medical image. The tomographic image data may be generated by at least one of computational x-ray tomography, medical resonance imaging, ultrasound imaging, positron emission tomography, medical resonance diffusion tensor imaging or reconstructing a three-dimensional image volume from the rotational image data.

In a (for example fourth) exemplary step, electrode orientation data is determined which describes a rotational orientation of the electrode in a reference system of the tomographic medical image data (is defined. The electrode orientation data is determined based on the rotational image data and the tomographic image data and the rotational orientation data. For example, the rotational orientation of the electrode in the reference system of the optimal two-dimensional medical image (in which positions defining the image contents of the rotational image data are defined) is transformed into the reference system of the tomographic image data (in which positions defining the image contents of the tomographic image data are defined). Such a transformation is predetermined (for example, at least one of known or fixed) and is based on the predetermined (at least one of known or fixed) spatial relationship between the two reference systems. The transformation is for example a linear transformation and may be embodied by a matrix multiplication, and may be for example a transformation of bases between the two reference systems.

The method may in one example include steps of determining the position and orientation of the electrode in the reference system of the tomographic image data and determining whether the anatomical structure is covered by the directional characteristic of a predetermined contact of the electrode, i.e. by an electric field for electrically stimulating the anatomical structure having for example a predetermined field strength and spatial relationship relative to at least one of the position of the directional contact and the position of the anatomical structure. To that end, also the electrode template data comprising constructional data describing the predetermined (for example, at least one of known or fixed) geometry of the electrode (specifically, the spatial relationship between the orientation marker and the desired directional contact) may be acquired by the method and serve as basis for determining a spatial relationship between the directional contact and the position of the anatomical structure. The position of the anatomical structure may be defined by the geometric or physical centre of gravity of the anatomical structure. The method may then also determine the percentage of the whole volume of the anatomical structure covered by the electric field and whether this percentage is within a desired range for performing electric stimulation of the anatomical structure.

The method according to the first aspect for example comprises a step of determining projected image data. The projected image data is determined based on (for example, from) the tomographic medical image data and describes (for example defines or represents) a projected tomographic medical image which is generated (e.g. synthesized) from the tomographic image data from the imaging perspective (for example relative to the anatomical structure, specifically the position of the anatomical structure) associated with the optimal two-dimensional medical image. In other words, the projected tomographic medical image describes (for example shows or depicts) the anatomical structure at least within a predetermined limit (e.g. accuracy limit in the same (i.e. at least to a predetermined extent similar) appearance as the optimal two-dimensional medical image. The projected image data is for example determined by determining a transformation, for example a positional transformation, between a reference system of the the rotational image data (in which positions defining the image contents of the rotational image data are defined) defined and the reference system of the tomographic image data (in which positions defining the image contents of the tomographic image data are defined), and the electrode orientation data is then determined by applying the transformation to the rotational orientation described by the rotational orientation data. Such a transformation is predetermined (for example, at least one of known or fixed) and is based on the predetermined (at least one of known or fixed) spatial relationship between the two reference systems. The transformation is for example a linear transformation and may be embodied by a matrix multiplication, and may be for example a transformation of bases between the two reference systems.

Then, the method may comprise a step of determining projected orientation data. The projected orientation data describes (for example, defines or represents) the rotational orientation of the electrode in the reference system of the projected medical image. The projected orientation data is determined based on the projected image data and the rotational image data and the rotational orientation data, for example by transforming the previously determined rotational orientation of the electrode from the reference system of the two-dimensional medical image (in which positions defining the image contents of the rotational image data are defined) into to the reference system of the projected tomographic medical image (in which positions defining the image contents of the projected tomographic medical image are defined). Such a transformation is predetermined (for example, at least one of known or fixed) and is based on the predetermined (at least one of known or fixed) spatial relationship between the two reference systems. The transformation is for example a linear transformation and may be embodied by a matrix multiplication, and may be for example a transformation of bases between the two reference systems. Because the imaging perspective associated with the projected tomographic image is known, it is possible to transform the rotational orientation of the electrode in the projected tomographic image into the rotational orientation of the electrode in the entire set of tomographic medical images so that, for example in conjunction with known information about the geometry of the electrode, the orientation and for example also position of the electrode in the reference system of the tomographic image data can be determined. Therefore, the method according to the first aspect for example determines the electrode orientation data based on the projected orientation data and the projected image data.

In one example, the projected image data is determined for all imaging perspectives with which the series of two-dimensional medical images is associated, and the projected image data describes a projected tomographic medical image for each of the imaging perspectives, and wherein the projected orientation data is determined based on the projected tomographic medical image best matching the optimal two-dimensional image, which match is determined for example by at least one of:

comparing colour values (for example, grey values) between the optimal two-dimensional medical image and the projected tomographic medical images; then, for example, a correlation of the colour values may be established between the two images, possibly taking into account the spatial relationships of neighbouring image elements (such as pixels or voxels) and their associated colour values;

applying a fusion algorithm (an image fusion algorithm, for example a rigid or elastic fusion algorithm) to register the optimal two-dimensional medical image to each one of the projected tomographic medical images and selecting, from the projected tomographic medical images and for determining the projected orientation data, only the projected tomographic medical image associated with the best fusion result. The best fusion result can be defined by a metric calculated by the fusion algorithm which indicates a best correspondence between the data sets (for example, between geometric features such as image contents by comparing the correspondence between spatial relationships of constituents of the image contents of one image relative to one another on the one hand to spatial relationships of constituents of the image contents of another image relative to one another on the other hand).

In an example of the method according to the first aspect, the rotational image data and the tomographic image data have been generated by application of an x-ray-based imaging modality, for example the rotational image data has been generated applying rotational conventional x-ray imaging, for example rotational radiography, and the tomographic image data has been generated by applying computed x-ray tomography. Specifically, the correspondence between colour values (e.g. grey values) defining the image contents of the rotational image data and colour values (e.g. grey values) defining the image contents of the tomographic image data is predetermined (for example, at least one of known and fixed) and may be used as an input to the method according to the first aspect. Such a correspondence is generally known from the physics of x-ray absorption for certain materials such as biological tissue forming e.g. the anatomical structure.

In another example of the method according to the first aspect, the rotational image data has been generated by application of an x-ray-based imaging modality and the tomographic image data has been generated by applying an imaging modality not involving application of x-rays, for example the rotational image data has been generated applying rotational conventional x-ray imaging (such as in the preceding example) and the tomographic image data has been generated by applying magnetic resonance imaging or positron emission imaging (PET) or an ultrasound imaging (sonography) or magnetic resonance diffusion tensor imaging (MR-DTI). In order to make the colour values (e.g. grey values) defining the image contents of the rotational image data comparable to the colour values (e.g. grey values) defining the image contents of the tomographic image data comparable, a mapping between the two different colour value scales associated with the rotational image data and the tomographic image data, respectively, may in one example be input to the method. Such a mapping may be included in atlas data describing a multi-modal atlas of the anatomical structure.

In this example, the method may therefore comprise the following steps:

acquiring atlas data describing a model (for example, an image-based model) of the anatomical structure and information about an image appearance of the anatomical structure in the imaging modality not involving application of x-rays and in the x-ray-based tomographic imaging modality (defined for example by colour values such as grey values defining the image constituents corresponding to the anatomical structure in both modalities), wherein the x-ray-based imaging modality is for example computed x-ray tomography;

determining, based on the tomographic image data and the atlas data, transformed appearance data describing an image appearance of the anatomical structure in the x-ray-based tomographic imaging modality (defined for example by colour values such as grey values defining the image constituents corresponding to the anatomical structure in the x-ray-based tomographic imaging modality).

The electrode orientation data may then be determined further based on the transformed appearance data and for example the projected image data may then be determined further based on (for example, from) the transformed appearance data.

The atlas data may describe a multimodal atlas of the anatomical structure in which models of the anatomical body parts are stored which have been generated with each a different imaging modality, and a transformation rule between anatomically corresponding parts of the models. That allows for a transformation of the tomographic image data into an imaging modality which is different from the one which was used for its generation, for example to make the medical image data comparable to that different imaging modality. The transformation rule may be based on tissue class information stored for each model which describes the image appearance (e.g. colour value such as a multi-colour value or a greyscale value) of the constituents of the anatomical body part in the respective imaging modality.

Furthermore, the atlas data may have been generated from medical images of the anatomical structure of a plurality of patients. Alternatively, the atlas data may have been generated from at least one medical image of the anatomical structure of only the specific patient for whom the rotational image data and the tomographic image data was generated, i.e. the model may be part of a patient-specific atlas.

The atlas data comprises for example positional information defined in a three-dimensional coordinate system (representing the reference system used for defining positional information contained in the atlas data). For example, the atlas data has been generated from tomographic images of the anatomical structure.

The transformed appearance data may be determined by matching the atlas data with the tomographic image data, for example by determining a transformation, for example a positional transformation, between a reference system of the tomographic image data (in which positions defining the image contents of the tomographic image data are defined) and a reference system of the atlas data (in which positions defining the image contents of the atlas data are defined) or by conducting for example a colour value match (such as grey value match) between the tomographic image data and the atlas data. The positional transformation may be predetermined (for example, at least one of known or fixed) or established as part of the method according to the first aspect for example by applying a fusion algorithm (such as a rigid or elastic fusion algorithm (to the tomographic image data and the atlas data).

In one example of the method according to the first aspect, the electrode comprises at least two directional contacts which are spaced apart from another, and wherein an image appearance of at least part of each of at least two spaces in between the at least two directional contacts in the two-dimensional medical images is used to verify the rotational orientation described by the rotational orientation data.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer is operably coupled to the program storage medium according to the third aspect for executing the program stored on the program storage medium.

In a fifth aspect, the invention is directed to a (physical, for example electrical, for example technically generated) signal wave, for example a digital signal wave, carrying information which represents the program according to the second aspect.

In a sixth aspect, the invention is directed a medical system for determining an orientation of an electrode, the electrode being configured for electrically stimulating an anatomical structure of a patient and comprising a rotational orientation marker, the system comprising:

a) the at least one computer according to the preceding claim; and b) at least one electronic data storage device storing at least one of the rotational image data or the tomographic image data or, as far as applicable, the atlas data,
   wherein the at least one computer is operably coupled to the at least one electronic data storage device for acquiring, from the at least one data storage device, at least one of the rotational image data or the tomographic image data or, as far as applicable, the atlas data.

In an example, the system according to the sixth aspect further comprises the two-dimensional medical imaging apparatus, wherein the two-dimensional medical imaging apparatus is operably coupled to the at least one computer for allowing the at least one computer to receive, from the two-dimensional medical imaging apparatus, at least one electronic signal corresponding to the rotational image data.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of therapy or surgery. More particularly, the invention does not involve or in particular comprise or encompass any surgical or therapeutic activity. The invention is instead directed as applicable to reading and processing data and operating or controlling a computer to execute a program which causes the computer to perform the data processing method according to the first aspect. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web).

For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method in accordance with the first aspect, which in the illustrative example of FIG. 1 starts with a step S1.1 of acquiring the rotational image data. In subsequent step S1.2, the rotational orientation data is determined. Step S1.3 then continues with acquiring the tomographic image data, followed by step S1.4 which encompasses determining the electrode orientation data on the basis of the data acquired and determined in preceding steps S1.1. to 1.3.

FIG. 2 shows a directional DBS electrode 1 (also called lead) comprising a cylindrical and elongate body on which contacts 2 are disposed. The contacts 2 include directional contacts 8 which do not run along the whole circumference of the base body but are designed to emit an electric field only in a three-dimensional sector spanning less than 360° degrees of the circumference. In the example of FIG. 2, the directional contacts 8 each cover at least substantially about 60° of the circumference and divided from one another by slits 7 which form spaces between the directional contacts 8. The spaces may be empty or filled with non-conductive material, for example the material of which the body of the electrode 1 is made. The slits 7 run parallel to the longitudinal axis of the body of the electrode 1 and therefore lie on a generatrix of the cylinder forming the basic shape of the electrode 1. The electrode 1 also comprises an orientation marker 3 comprising a marker band having a first part 5 and a second part 4 and a marker window 6. The rotational orientation of the orientation marker is defined as a vector pointing in a direction to the exterior of the body of the electrode 1 and oriented perpendicular to the surface of the centre of the first part 5, i.e. having its base in a point lying in the mirror plane of symmetry of the first part 1 in which also the longitudinal axis of the body of the electrode lies. The marker band is made of platinum (Pt) or at least of a material (such as an alloy). comprising platinum (Pt), and is more radiopaque than the marker window 6. In one example, the marker band is also more radiopaque than the body of the electrode 1. The optimal two-dimensional medical image is a radiography in which the depiction (image appearance) of the first part 5 is the thinnest, i.e. is defined by the smallest number of image elements (such as pixels), among the two-dimensional medical images.

As shown in FIG. 3, the rotational image data may be acquired by imaging the anatomical structure in the patient's body by using a C-arm x-ray apparatus. Then, the image depiction of the electrode 1 (lead) is extracted from the two-dimensional medical images (2D x-ray images/radiographies), for example by applying a segmentation algorithm to the two-dimensional medical images. In the box in the lower left-hand corner of FIG. 3 the rightmost two-dimensional medical image is chosen as the optimal two-dimensional medical because it contains the thinnest depiction of the first part 5 of the marker band. As indicated by the arrow in that box, the rotational orientation of the electrode 1 (and therefore the orientation marker 3) is determined to lie in the image plane of the rightmost two-dimensional medical image and point to the lower right of that image.

Figure 3:
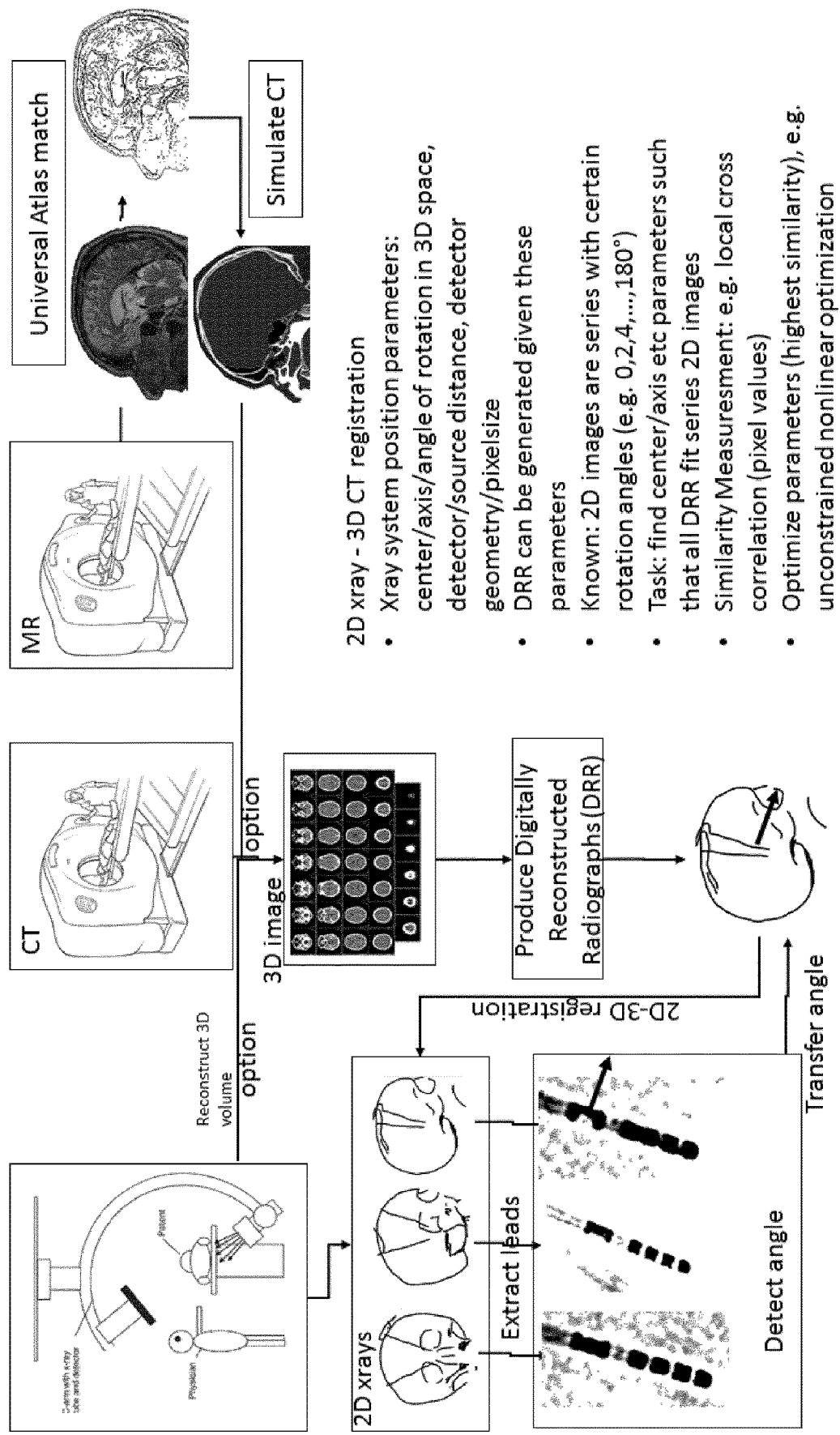
FIG. 3 illustrates an embodiment of the disclosed method according to the first aspect.

As also shown in FIG. 3, a 3D (three-dimensional) image corresponding to the tomographic image data or the transformed appearance data is acquired. The tomographic image data may be generated either by CT or reconstruction of a 3D image from the 2D x-ray-images. Alternatively or additionally, the 3D image may be acquired on the basis of an MR tomography which has been transformed into a CT appearance, thereby generating the transformed appearance data which also is a three-dimensional image data set. The transformation of the MR tomography embodies the tomographic image data and is transformed into CT grey values by acquiring multi-modal atlas data and conducting a match between the atlas data and the MR tomography. The match is called universal atlas match in FIG. 3. Based on the correspondence between a tissue-dependent MR grey value scale and a tissue-dependent CT grey value scale contained in the atlas, a CT (computed x-ray tomography) is simulated from the MR tomography by replacing the grey values of the MR tomography (e.g. voxel-wise) with the grey values of a corresponding CT image.

From the 3D image, digitally reconstructed radiographs (DRRs) are produced. In one example, only on DRR is produced from the perspective towards the anatomical structure corresponding to the perspective associated with the optimal two-dimensional medical image. In another example, DRRs are generated for all perspective for which a two-dimensional medical image has been acquired or generated. Then, the DRR best matching the optimal two-dimensional medical image is selected for further processing. A transformation (called 2D-3D registration in FIG. 3) between the reference system of the 2D images and the DRR or DRRs is established, for example by fusing the image data sets to on another. Based on that transformation, the rotational orientation of the electrode can be determined in the reference system of the 2D x-ray images based on knowledge of the imaging perspective relative to the anatomical structure associated with (i.e. used when) generating the 2D x-ray images. The rotational orientation can then be transformed from the reference system of the 2D x-ray images into the reference system of the DRR or DRRs by applying the 2D-3D registration. Based on the knowledge of the imaging perspective used for generating the DRR or DRRs, the rotational orientation of the electrode can then be determined in the reference system of the 3D image, as shown in the upper half of FIG. 4. The rotational orientation thus determined can then be compared for example to a predetermined (e.g. desired) rotational orientation of the electrode, for example in the reference system of the 3D image. If the determined rotational orientation is at least within a predetermined distance substantially equal to the predetermined rotational orientation, the envisaged medical procedure may start as desired. If the determined rotational orientation is not at least within a predetermined distance substantially equal to the predetermined rotational orientation, the rotational orientation of the electrode may be adjusted until agreement with the predetermined rotational orientation is found.

Figure 1:
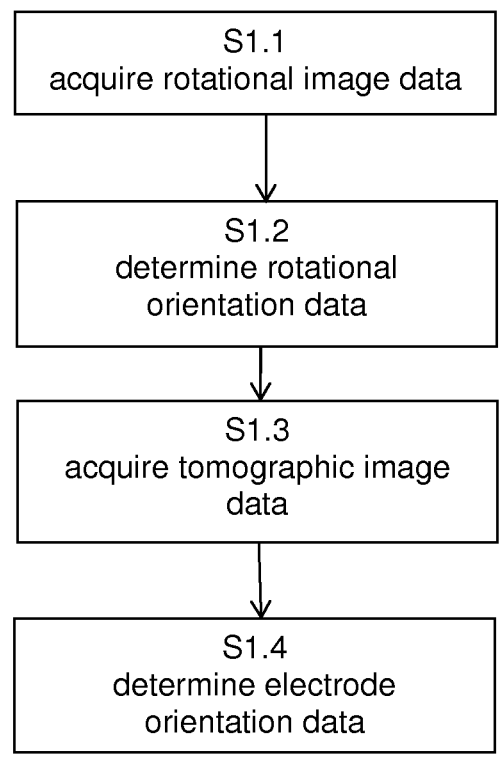
FIG. 1 is a flow diagram showing the basic steps of the disclosed method according to the first aspect.
Figure 2:
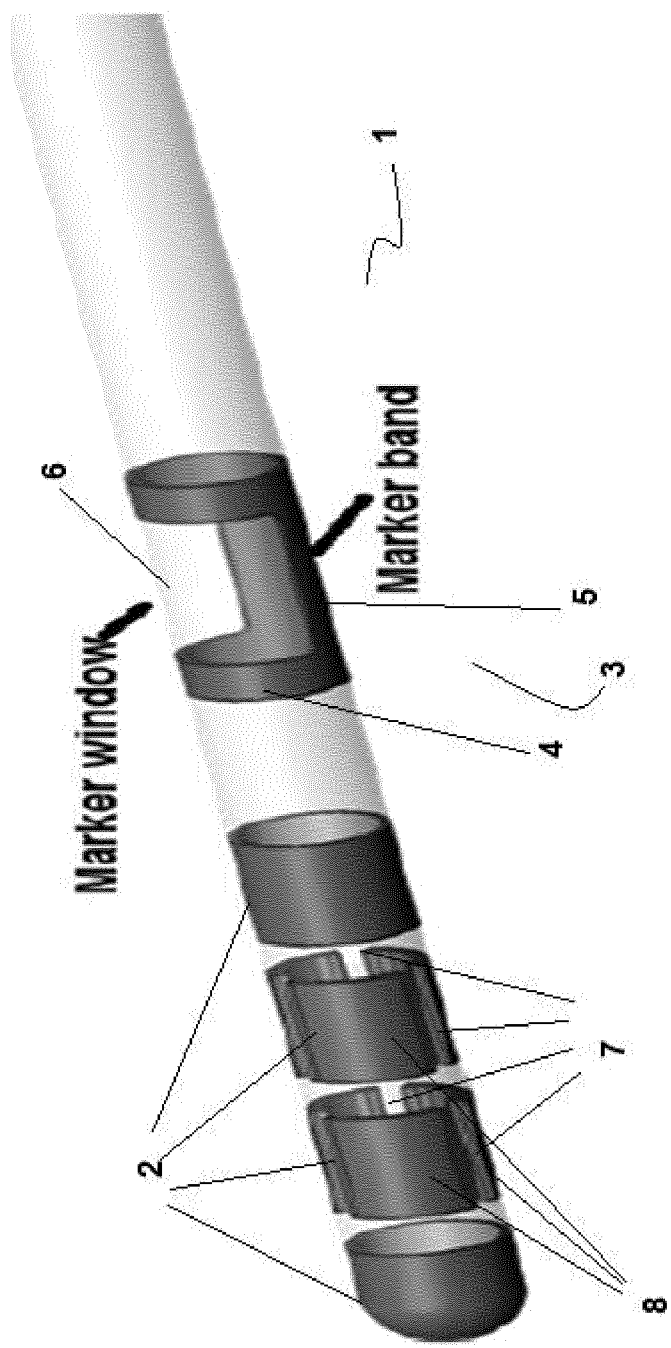
FIG. 2 shows a directional DBS electrode with a directional marker.
Figure 4:
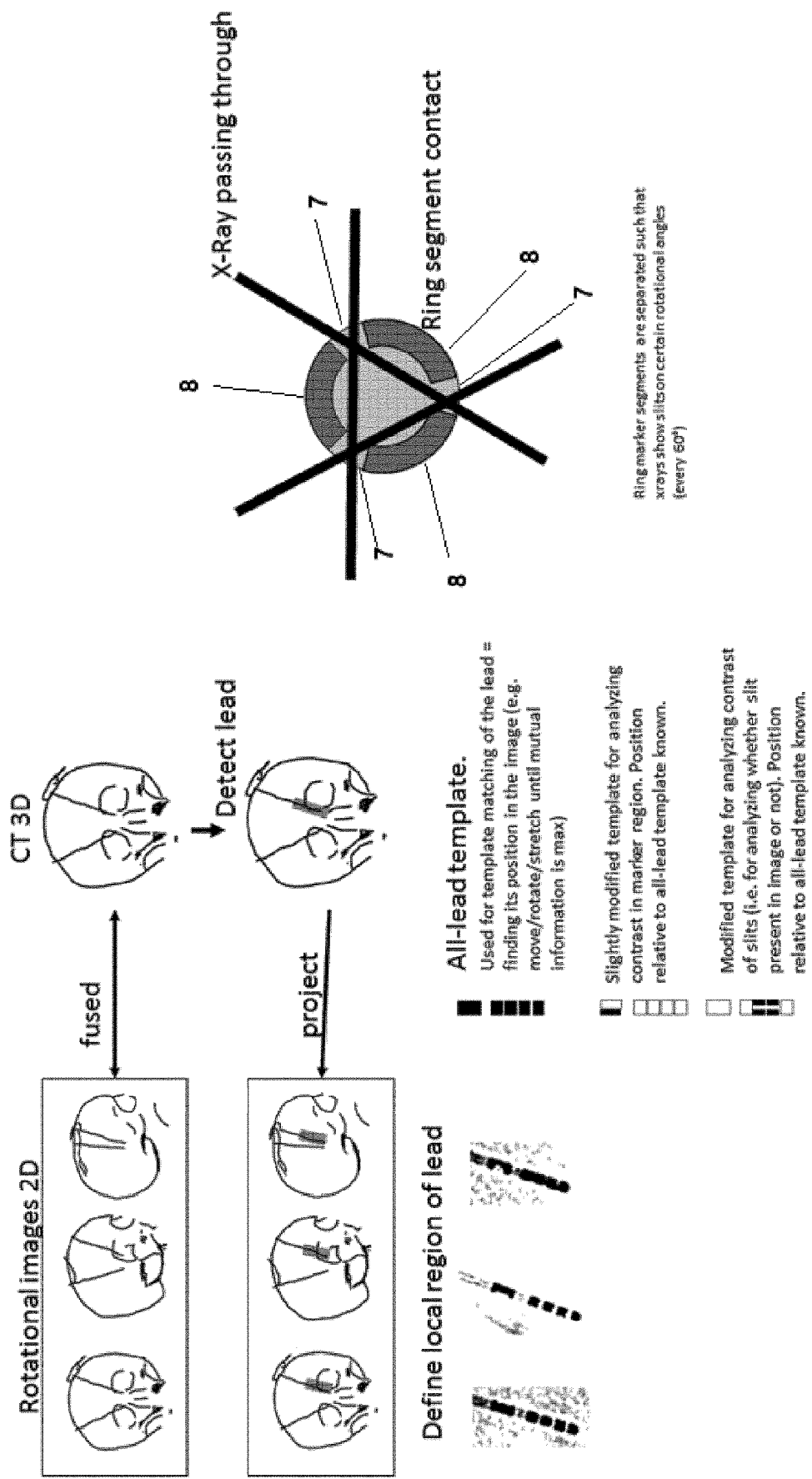
FIG. 4 illustrates a specific approach to determining the rotational orientation of the electrode from the two-dimensional medical images.

As shown in FIG. 4, the slits 7 between directional contacts 8 may be used for supporting determination of the rotational orientation, for example to verify the result received from analyzing the two-dimensional medical images with regard to the image appearance of the orientation marker. The right part of FIG. 4 illustrates that if an x-ray used for generating the two-dimensional medical image may with a finite probability pass through two slits 7 and thus generate a corresponding mark in the two-dimensional image because the material of which the directional contacts 8 are made is differs in radio-opacity from the material of which the slits 7 are made or with which they may be filled. For example, an x-ray passing through two slits 7 may produce a mark indicating translucence compared to the image appearance of the directional contacts 8. Thereby, an additional indication may be received with an accuracy of about 60° in the example of FIGS. 1 and 4 whether the rotational orientation determined from the image appearance of the orientation maker is valid or not.

The disclosed method may further be summarized as follows.

The method uses images taken by an x-ray system while rotating around an anatomical structure such as the patient's head. A 3D (volumetric) image of the head from any tomographic scanner may be used. Further, an algorithm is used for registering the 2D x-ray images to the 3D image. Another algorithm detects the lead(s) in the 2D x-ray images and defines the angle of the lead's orientation marker with respect to the image plane (i.e. with respect to the reference system of the 2D x-ray images). The angle information is mapped back from 2D image space into 3D image (anatomy) space by means of the registration. The computer system is able to show a simulated projection of the 3D image blended on any of the 2D x ray images modulo the calculated registration in order to allow the user for a quick check of registration precision.

Several embodiments are considerable:
Work with one x-ray, two x-ray or multiple (rotational) x-rays. The more images are used, the more robust is the determination of the angle
Use standard CT as a 3D image. They are calibrated to Hounsfield values. Digitally reconstructed radiographs (DRR) can be calculated from scratch.
Use reconstructed CT directly from the x-Ray scanner as 3D image. Then no additional scan is necessary. Recalibration to HU values may be necessary and can be done with help of Universal Atlas
Use pre-operative MRI as a 3D image. Then this needs to be preprocessed and transformed into Hounsfield values of a corresponding CT representation. This can be done with help of the Universal Atlas.
The calculation of the digitally reconstructed radiographs (DRRs) can be done on graphics card.
The directional lead has slits between the segmented contacts which are visible in x-rays at certain angles. These can be used additionally in order to improve angle precision.
Leads can be either segmented by an algorithm in the x-rays or in the 3D image.
Marker orientation can be found by template matching or by machine learning.
Camera parameters (such as the imaging perspective) of the 2D x-ray images may be taken from DICOM information stored together/associated with the x-ray image information.
If not available from DICOM, camera parameters of X-Rays are estimated e.g. from lead geometry in 2D images.
Aside from the rotational orientation, also the lead type may be detected in x-rays (manufacturer, model), for example based on comparison of the image appearance of at least part of the electrode (such as the orientation marker) with the electrode template data.

The disclosed method aims for a quick and traceable transfer of information on DBS lead orientation from 2D images into 3D anatomy. It is quick because the system contains an automatic algorithm which allows for registering 2D and 3D coordinates which otherwise would be a cumbersome step needed to be done by the user manually (i.e. manual adoption of several degrees of freedom like shift/rotation/zoom/focus length in order to match 2D and 3D images). Furthermore, the 2D-3D registration makes the final angle assignment traceable for the user. He can immediately check that the calculated angle makes sense in relation to both 2D and 3D image.

The invention claimed is:
1. A computer-implemented method for determining an orientation of an electrode, the electrode being configured for electrically stimulating an anatomical structure of a patient and comprising a rotational orientation marker, the method comprising executing, on at least one processor of at least one computer, steps of:
acquiring, by the at least one processor, rotational image data describing two-dimensional medical images of the anatomical structure and the electrode, the two-dimensional medical images having been taken with a two-dimensional medical imaging apparatus during rotation of the medical imaging apparatus relative to the anatomical structure, the rotational image data further describing, for each of the two-dimensional medical images, an imaging perspective relative to the anatomical structure associated with the respective two-dimensional medical image and including at least two different imaging perspectives obtained during rotation of the medical imaging apparatus relative to the anatomical structure;
wherein in a cross section of the electrode taken perpendicular to a longitudinal axis of the electrode, the at least two directional contacts form ring segments with one or more less radio-opaque portions disposed in between the at least two directional contacts;

wherein the at least two imaging perspectives are defined relative to the anatomical structure by an x-ray passing through the one or more less-radio-opaque portions to produce a mark indicating translucence compared to an image appearance of the at least two directional contacts;

determining, by the at least one processor and based on the rotational image data, rotational orientation data describing the rotational orientation of the electrode in a reference system of the two-dimensional medical images;

acquiring, by the at least one processor, tomographic image data describing a set of tomographic medical images of the anatomical structure, the tomographic image data representing previously acquired three dimensional medical images representing the anatomical structure in a three dimensional reference system; and, determining, by the at least one processor and based on the rotational image data and the tomographic image data and the rotational orientation data, electrode orientation data describing a rotational orientation of the electrode in the three dimensional reference system of the tomographic image data.

2. The method according to claim 1, further comprising:

acquiring, by the at least one processor, predetermined orientation data describing a predetermined rotational orientation of the electrode in the reference system of the two-dimensional medical images;

determining, based on the rotational orientation data and the predetermined orientation data, optimal orientation data describing the two-dimensional medical image associated with a rotational orientation of the electrode in the reference system of the two-dimensional medical image fulfilling a predetermined condition in relation to the predetermined rotational orientation, the two-dimensional medical image herein forth being called the optimal two-dimensional medical image;

determining, by the at least one processor and based on the tomographic medical image data, projected image data describing a projected tomographic medical image generated from the tomographic medical image data from the imaging perspective associated with the optimal two-dimensional medical image; and, determining, by the at least one processor and based on the projected image data and the rotational image data, projected orientation data describing the rotational orientation of the electrode in the reference system of the projected medical image.

3. The method according to claim 2, wherein the electrode orientation data is determined, by the at least one processor, based on the projected orientation data and the projected image data.

4. The method according to claim 2, wherein the projected image data is determined for each of the imaging perspectives with which the series of two-dimensional medical images is associated, and the projected image data describes a projected tomographic medical image for each of the imaging perspectives, and wherein the projected orientation data is determined based on the projected tomographic medical image best matching the optimal two-dimensional medical image, which match is determined by at least one of:

comparing colour values between the optimal two-dimensional medical image and the projected tomographic medical images;

applying a fusion algorithm to register the optimal two-dimensional medical image to each one of the projected tomographic medical images and selecting, from the projected tomographic medical images and for determining the projected orientation data, only the projected tomographic medical image associated with the best fusion result.

5. The method according to claim 1, wherein determining the rotational orientation data includes determining, by the at least one processor and based on the rotational image data, an image appearance of the rotational orientation marker, by at least one of:

segmenting an image appearance of the electrode in each of the two-dimensional medical images;

edge detection of constituents of the two-dimensional medical images;

comparing the image appearance of the electrode in the two-dimensional medical images to previously acquired and predetermined electrode template data describing constructional data of the electrode.

6. The method according to claim 1, wherein each two-dimensional medical image is associated with a different imaging perspective.

7. The method according to claim 2, wherein determining the projected medical image data includes determining a transformation between a reference system in which the rotational image data is defined and the reference system in which the tomographic image data is defined, and wherein determining the electrode orientation data includes applying the transformation to the rotational orientation described by the rotational orientation data.

8. The method according to claim 1, wherein the rotational image data and the tomographic image data have been generated by application of an x-ray-based imaging modality.

9. The method according to claim 1, wherein the rotational image data has been generated by application of an x-ray-based imaging modality and the tomographic image data has been generated by applying an imaging modality not involving application of x-rays.

10. The method according to claim 2, further comprising:

acquiring, by the at least one processor, atlas data describing a model of the anatomical structure and information about an image appearance of the anatomical structure in the imaging modality including by applying magnetic resonance imaging or positron emission imaging (PET) or an ultrasound imaging (sonography) or magnetic resonance diffusion tensor imaging (MR-DTI) and in an x-ray-based tomographic imaging modality, wherein the x-ray-based tomographic imaging modality is computed x-ray tomography;

determining, by the at least one processor and based on the tomographic image data and the atlas data, transformed appearance data describing an image appearance of the anatomical structure in the x-ray-based tomographic imaging modality; and, wherein the electrode orientation data is determined further based on the transformed appearance data, the projected image data is determined further based on the transformed appearance data.

11. The method according to claim 10, wherein determining the transformed appearance data includes matching the atlas data with the tomographic image data.

12. The method according to claim 2, wherein the projected medical image is a digitally reconstructed radiograph.

13. A non-transitory computer program which, when running on at least one processor of at least one computer causes the at least one computer to perform the steps of:
- acquire, by the at least one processor, rotational image data describing two-dimensional medical images of an anatomical structure and an electrode, the two-dimensional medical images having been taken with a two-dimensional medical imaging apparatus during rotation of the medical imaging apparatus relative to the anatomical structure,
- the rotational image data further describing, for each of the two-dimensional medical images, an imaging perspective relative to the anatomical structure associated with the respective two-dimensional medical image and including at least two different imaging perspectives relative to the anatomical structure obtained during rotation of the medical imaging apparatus relative to the anatomical structure;
- wherein in a cross section of the electrode taken perpendicular to a longitudinal axis of the electrode, the at least two directional contacts form ring segments with one or more less radio-opaque portions disposed in between the at least two directional contacts;
- wherein the at least two imaging perspectives are defined relative to the anatomical structure by an x-ray passing through the one or more less radio-opaque portions to produce a mark indicating translucence compared to an image appearance of the at least two directional contacts;
- determine, by the at least one processor and based on the rotational image data, rotational orientation data describing the rotational orientation of the electrode in a reference system of the two-dimensional medical images;
- acquire, by the at least one processor, tomographic image data describing a set of tomographic medical images of the anatomical structure, the tomographic image data representing previously acquired three dimensional medical images representing the anatomical structure in a three dimensional reference system; and,
- determine, by the at least one processor and based on the rotational image data and the tomographic image data and the rotational orientation data, electrode orientation data describing a rotational orientation of the electrode in the three dimensional reference system of the tomographic image data.

14. A medical system for determining an orientation of an electrode, the electrode being configured to electrically stimulating an anatomical structure of a patient and comprising a rotational orientation marker, the system having at least one processor with associated memory, the memory having instructions for the at least one processor to:
- acquire, by the at least one processor, rotational image data describing two-dimensional medical images of the anatomical structure and the electrode, the two-dimensional medical images having been taken with a two-dimensional medical imaging apparatus during rotation of the medical imaging apparatus relative to the anatomical structure,
- wherein in a cross section of the electrode taken perpendicular to a longitudinal axis of the electrode, the at least two directional contacts form ring segments with one or more less radio-opaque portions disposed in between the at least two directional contacts;
- wherein the at least two imaging perspectives are defined relative to the anatomical structure by an x-ray passing through the one or more less radio-opaque portions to produce a mark indicating translucence compared to an image appearance of the at least two directional contacts;
- the rotational image data further describing, for each of the two-dimensional medical images, an imaging perspective relative to the anatomical structure associated with the respective two-dimensional medical image and including at least two different imaging perspectives relative to the anatomical structure obtained during rotation of the medical imaging apparatus relative to the anatomical structure;
- determine, by the at least one processor and based on the rotational image data, rotational orientation data describing the rotational orientation of the electrode in a reference system of the two-dimensional medical images;
- acquire, by the at least one processor, tomographic image data describing a set of tomographic medical images of the anatomical structure, the tomographic image data representing previously acquired three dimensional medical images representing the anatomical structure in a three dimensional reference system; and,
- determine, by the at least one processor and based on the rotational image data and the tomographic image data and the rotational orientation data, electrode orientation data describing a rotational orientation of the electrode in the three dimensional reference system of the tomographic image data.

15. The system according to claim 14, further comprising the two-dimensional medical imaging apparatus, wherein the two-dimensional medical imaging apparatus is operably coupled to the at least one processor for allowing the at least one processor to receive, from the two-dimensional medical imaging apparatus, at least one electronic signal corresponding to the rotational image data.

* * * * *